Figure 1:
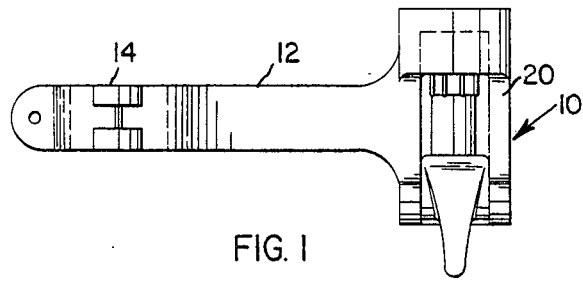

United States Patent [19]

Drury

[11] 4,074,900
[45] Feb. 21, 1978

[54] DENTAL AMALGAM CAPSULE HOLDER

[75] Inventor: Frederick H. Drury, Winterburn, Canada

[73] Assignee: Weatherford Oil Tool Company, Ltd., Edmonton, Canada

[21] Appl. No.: 758,511

[22] Filed: Jan. 11, 1977

[30] Foreign Application Priority Data

Nov. 3, 1976 Canada .................................. 264839

[51] Int. Cl.² .............................................. B25B 5/04
[52] U.S. Cl. ................................ 269/254 R; 366/210; 366/602
[58] Field of Search ................. 259/72, 1 R, DIG. 20, 259/91, 75, 12, 29, 13, 35, 17, 54, 56, 59; 269/238, 254 CS, 287, 288, 254 R; 337/190, 194, 195, 234; 403/33, 327, 328, 330

[56] References Cited

U.S. PATENT DOCUMENTS

| 1,747,378 | 2/1930 | McClure ...................... 259/DIG. 20 |
| 3,259,563 | 7/1966 | Monica .......................... 269/254 CS |
| 3,749,390 | 7/1973 | Schubert ...................... 259/DIG. 20 |
| 3,917,062 | 11/1975 | Winters ................................. 259/72 |

Primary Examiner—Robert W. Jenkins
Attorney, Agent, or Firm—Beveridge, DeGrandi, Kline & Lunsford

[57] ABSTRACT

A capsule holder for a dental amalgamator which holds a capsule firmly for high speed amalgamation but which allows easy insertion and removal. The holder has a body with a spring containing cavity at one end capable of receiving a first end of a capsule when this is inserted at an angle to the axis of the recess, and at the other end of the body there is provided a pivotable retainer for the second end of the capsule. The retainer has a concave surface which in a first position of the retainer receives the second end of the capsule when the first end has been inserted into the cavity with little compression of the spring, and the retainer is pivotable in an over-center manner to move the capsule against the spring force and into a second position in which the capsule is held firmly between the spring and the retainer, the retainer being prevented from moving beyond this second position.

11 Claims, 4 Drawing Figures

U.S. Patent  Feb. 21, 1978  4,074,900

DENTAL AMALGAM CAPSULE HOLDER

The present invention relates to a capsule holder for a dental amalgamator.

Dental amalgamators for mixing amalgam constituents are known, which include a capsule holder capable of holding a capsule containing the amalgam, and having a mechanism for rapidly vibrating the capsule holder to mix the amalgam. Commonly, the capsule holder is vibrated on one end of an arm the other end of which is carried by a collar surrounding and moved by a cam or eccentric. Also, the capsule holder may be mounted directly on a vibrating member as for example in U.S. Pat. No. 3,379,390, issued July 31, 1973 to Pennwalt Corp.

In the past, capsule holders have generally included spring arms such as can be sprung apart to receive the ends of a capsule between detents at the ends of the arms, reliance being placed on the spring force of the arms for keeping capsules in place. Such arrangements are shown for example in Canadian Pat. Nos. 806,918 and 821,406, both issued to Thiel and Michaels, respectively on Feb. 25 and Aug. 26, 1969. However, with the coming of high speed amalgamators, there is a need for holding the capsule more firmly then provided in these arrangements, while also still allowing the capsule to be easily inserted and removed from the holder. Spring arms are liable to break if easily opened, but, it made strong enough to prevent breakage, may be difficult to open.

In accordance with one aspect of the invention, a capsule holder for use on a vibrator comprises a body having a first locating means for receiving a first end of a capsule while spring means associated therewith maintains an outwards force on said first end, the locating means allowing pivotable movement of the capsule during its insertion therein, and the body having pivot means displaced from said first locating means carrying second locating means pivotable from a first position in which the ends of a capsule may be inserted between the two locating means with little compression of the spring, through a dead center position in which the ends of the capsule are aligned with the pivot, to a second position in which the spring means are compressed and hold the capsule firmly against the second locating means which latter means are prevented from moving beyond this second position.

Figure 2:
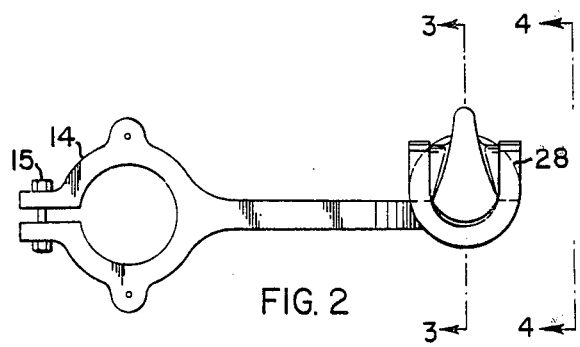
Figures 3, 4:
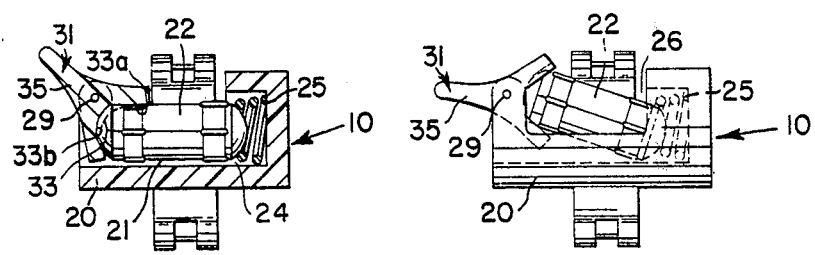

The invention will be more fully described with reference to the accompanying drawings, in which:

FIGS. 1 and 2 respectively show plan and side views of the holder and associated parts, FIG. 3 shows a sectional view on lines 3—3 of FIG. 2, with the capsule fully inserted into place, and FIG. 4 shows an end view of the holder, on lines 4—4 of FIG. 2, during insertion of a capsule.

Referring firstly to FIGS. 1 and 2, these show a capsule holder 10 the main body part of which is integrally molded of plastics material with an arm 12 and a collar 14. The collar 14 is intended to be rotably fitted, with the help of an adjustment screw 15, onto a cam which is of known form, and which is mounted on a high speed drive shaft, at an angle to this shaft, so that rotation of the cam causes to and fro motion of the capsule holder as indicated in FIG. 1, together with a slight rocking motion when viewed end-wise as in FIGS. 3 and 4. This cam mechanism is conventional and will not be described in detail.

The holder 10, as best seen in FIG. 3, comprises a body part 20 of integral construction and which is of generally cylindrical form, having a co-axial cylindrical recess indicated at 21, and which receives a capsule 22 having two identical rounded ends. The recess is closed at one end to provide a cavity 24, and is provided with conical compression spring 25 the larger end of which is a forced fit into the cavity, the recess and spring providing locating means for one rounded end of the capsule. The body part 20 has a cut-away area 26, best seen in FIG. 4, the lower surface of which is coincident with the diametral plane of the body 20 and the recess, so that the recess is open along most of its upper side. This open part allows insertion of the capsule by pivoting into the position shown after the first end has been located against spring 25.

At the end of the body part remote from the cavity 24, the material of the body part is extended upwardly on each side of the recess to provide integral extensions 28, which receive a transverse pivot pin 29 which is located well above the central axis of the body member and recess, so as to be about at the same level, when viewed as in FIG. 3, with the top of the cavity 24.

The pivot pin 29 receives a pivotable retainer element 31. This element has an inwardly facing concave surface 33, best seen in FIG. 3, which, when seen in the sectional plane of FIG. 3, curves through more than 90°, so that when in the position of FIG. 3 an upper portion 33a of this surface can rest against the upper surface of a capsule, while another portion 33b of this surface holds one end of the capsule while the other end is pressed against the compression spring 25. The surface 33a thus limits rotation of the retainer element 31 in the clockwise direction as shown in FIG. 3. The retainer element also includes a lug or projection 35, which is conveniently shaped for operation by a person's thumb. A downwards force on this projection pivots the retainer element in the anit-clockwise direction, moving the capsule firstly inwardly against the spring 25, until a dead center position is reached in which the ends of the capsule are aligned with pivot 29, whereupon further movement of the retainer allows the capsule to reach the position shown in FIG. 4 and then to be easily released.

It will be evident from the above that this arrangement allows the capsule to be held very firmly by a relatively strong spring 25, which maintains an outwards force on the end of the capsule, while allowing release of the capsule by operation of the projection 35 which acts as a lever giving a mechanical advantage in the compression of the spring. For insertion of the capsule, the retainer element 31 is rotated into the position shown in FIG. 4, and one end of the capsule is inserted in the cavity 24 and, with very slight compression of the spring, the other end is inserted under the surface 33a of the retainer element. From there, the capsule is easily moved into the operative position of FIG. 3 by downwards pressure on the outer end of the capsule, and retained there by virtue of the over-centre movement of retainer 31. Release is easily achieved, as indicated, by pressing downwardly on the projection 35.

The preferred material for the holder is a glass filled nylon. However, the holder may be formed of metal, preferably aluminum. Also, although in the preferred arrangement described, the body part 10 has an axis perpendicular to arm 12, the body part may be in line with the arm, depending on machine design. In any case, it will be clear that arm 12 can be made strong enough to prevent breakage without affecting the ease of insertion of a capsule.

I claim:

1. A capsule holder for use on a vibrator comprising a body having first locating means for receiving a first end of a capsule while spring means associated with said locating means maintains an outwards force on said first end of the capsule, said locating means allowing pivotal movement of the capsule during its insertion therein, said body having pivot means displaced from said first locating means and carrying second locating means for the second end of the capsule, said second locating means being pivotable from a first position in which the ends of a capsule may be inserted between said two locating means with little compression of the spring means, through a dead center position in which the ends of the capsule are aligned with said pivot means, and to a second position in which the spring means hold the capsule firmly against the second locating means which latter means are prevented from moving beyond said second position.

2. A capsule holder according to claim 1 wherein said second locating means has a projection to assist its manipulation.

3. A capsule holder according to claim 1, wherein said second locating means includes a concave surface for engagement with the second end of the capsule, said surface curving in one plane through at least 90° whereby, in the said second position, one portion of said surface rests against the side of the capsule to limit pivotable movement beyond said second position, while another portion of said surface holds said second end of the capsule.

4. A capsule holder according to claim 1, wherein said body is integrally formed with an arm carrying a collar suitable for movement by a cam or eccentric.

5. A capsule holder according to claim 1, wherein said body is integrally formed with an arm carrying a collar suitable for movement by a cam or eccentric, said arm extending transversely of an axis of said body coinciding with an axis of a capsule when held firmly in said holder.

6. A capsule holder for use on a vibrator comprising a body having an elongated recess, said recess being open along part of one side and closed at one end, said closed end being provided with a compression spring and providing first locating means locating a first end of a capsule while permitting insertion of the capsule by pivoting through the open side of the recess, pivot means carried by said body disposed transversely of the recess and in a position displaced from the closed end of the recess and also displaced from a central axis of the recess towards the open side thereof, said pivot means carrying second locating means for the second end of the capsule, said second locating means being pivotable from a first position in which the ends of a capsule may be inserted between said two locating means with little compression of the spring, through a dead center position in which the ends of the capsule are aligned with said pivot means, and to a second position in which the spring means are compressed and hold the capsule firmly against the second locating means which latter means are prevented from moving beyond said second position.

7. A capsule holder according to claim 6, wherein said body is of molded plastics material, and wherein said pivot means are carried by integral extensions of said body projecting from the open side of the recess at the end of the body remote from the closed end of the recess.

8. A capsule holder according to claim 6, wherein said second locating means has a projection to assist its manipulation.

9. A capsule holder according to claim 6, wherein said second locating means includes a concave surface for engagement with the second end of the capsule, said surface curving in one plane through at least 90° whereby, in the said second position, one portion of said surface rests against the side of the capsule to limit pivotable movement beyond said second position, while another portion of said surface holds said second end of the capsule.

10. A capsule holder according to claim 6, wherein said body is integrally formed with an arm carrying a collar suitable for movement by a cam or eccentric.

11. A capsule holder according to claim 6, wherein said body is integrally formed with an arm carrying a collar suitable for movement by a cam or eccentric, said arm extending transversely of an axis of said body coinciding with an axis of a capsule when held firmly in said holder.

* * * * *